(12) United States Patent (10) Patent No.: US 9,982,002 B2
Chand et al. (45) Date of Patent: May 29, 2018

(54) SULFOXIDATION CATALYSTS AND METHODS FOR THEIR PREPARATION AND USE

(71) Applicant: INDIAN INSTITUTE OF TECHNOLOGY MADRAS, Chennai, Tamil Nadu (IN)

(72) Inventors: Dillip Kumar Chand, Chennai (IN); Rajan Deepan Chakravarthy, Coimbatore (IN)

(73) Assignee: INDIAN INSTITUTE OF TECHNOLOGY MADRAS, Chennai (IN)

( * ) Notice: Subject to any disclaimer, the term of this patent is extended or adjusted under 35 U.S.C. 154(b) by 15 days.

(21) Appl. No.: 15/029,945

(22) PCT Filed: Sep. 8, 2014

(86) PCT No.: PCT/IB2014/064308
§ 371 (c)(1),
(2) Date: Apr. 15, 2016

(87) PCT Pub. No.: WO2015/056117
PCT Pub. Date: Apr. 23, 2015

(65) Prior Publication Data
US 2016/0251388 A1 Sep. 1, 2016

(30) Foreign Application Priority Data
Oct. 15, 2013 (IN) .......................... 4639/CHE/2013

(51) Int. Cl.
*C07F 11/00* (2006.01)
*C07D 319/06* (2006.01)
(Continued)

(52) U.S. Cl.
CPC ......... *C07F 11/005* (2013.01); *B01J 31/0239* (2013.01); *B01J 31/2213* (2013.01);
(Continued)

(58) Field of Classification Search
CPC ... C07F 11/005; C07D 319/06; C07C 211/63; C07C 315/02; B01J 31/0239;
(Continued)

(56) References Cited

U.S. PATENT DOCUMENTS

2011/0011771 A1 1/2011 Litz et al.

FOREIGN PATENT DOCUMENTS

CN 101513619 A * 8/2009

OTHER PUBLICATIONS

Kowalski, P. et al. Oxidation of sulfides to sulfoxides. Part 2: Oxidation by hydrogen peroxide. Tetrahedron. 2005, vol. 61, p. 8322.*

(Continued)

*Primary Examiner* — Taylor V Oh

(57) ABSTRACT

Methods and compositions of catalysts for sulfoxidation reaction processes are disclosed. The sulfoxidation reaction process can be performed in an aqueous medium, and the catalysts can be recycled for further use. In some embodiments, a method of making a catalyst may include contacting a transition metal compound with an oxidizing agent to form a first solution, contacting a carboxylic acid compound with a cationic surfactant to form a second solution, mixing the first solution and the second solution to form a precipitate, and isolating the precipitate.

18 Claims, 6 Drawing Sheets

(51) Int. Cl.
*B01J 31/02* (2006.01)
*B01J 31/22* (2006.01)
*B01J 37/03* (2006.01)
*B01J 37/12* (2006.01)
*C07C 211/63* (2006.01)
*C07C 315/02* (2006.01)

(52) U.S. Cl.
CPC ....... *B01J 31/2239* (2013.01); *B01J 31/2295* (2013.01); *B01J 37/031* (2013.01); *B01J 37/12* (2013.01); *C07C 211/63* (2013.01); *C07C 315/02* (2013.01); *C07D 319/06* (2013.01); *B01J 2231/70* (2013.01); *B01J 2231/72* (2013.01); *B01J 2531/56* (2013.01); *B01J 2531/62* (2013.01); *B01J 2531/64* (2013.01); *B01J 2531/66* (2013.01); *B01J 2531/96* (2013.01)

(58) Field of Classification Search
CPC .......... B01J 31/2239; B01J 31/2213; B01J 31/2295; B01J 37/031; B01J 37/12; B01J 2231/70; B01J 2231/72; B01J 2531/056; B01J 2531/62; B01J 2531/64; B01J 2531/66; B01J 2531/96
USPC ............................................ 549/374; 556/57
See application file for complete search history.

(56) References Cited

OTHER PUBLICATIONS

Sato, K. et al. Oxidation of sulfides to sulfoxides and sulfones with 30% hydrogen peroxide under organic solvent- and halogen-free conditions. Pergamon. 2001, vol. 57, p. 2474.*
Growing Demand from China Drives Global Dimethyl Sulfoxide Demand to 40 Thousand Tons by 2012, According to New Report by Global Industry Analysts, Inc., accessed at http://web.archive.org/web/20080926043924/http://www.prweb.com/releases/dimethyl_sulfoxide/dmso/prweb844754.htm, accessed on Apr. 14, 2016, pp. 2.
What are DMSO and DMS? accessed at http://web.archive.org/web/20130930164845/http://www.gaylordchemical.com/index.php?page=what-is-dmso-dms, accessed on Apr. 14, 2016, pp. 3.
Bortolini et al., Metal catalysis in oxidation by peroxides. Anionic molybdenum-picolinate N-oxido-peroxo complex: An effective oxidant of primary and secondary alcohols in nonpolar solvents, Journal of Organic Chemistry (Nov. 1987), 52(24) pp. 5467-5469.
Chakravarthy et al., A molybdenum based metallomicellar catalyst for controlled and selective sulfoxidation reactions in aqueous medium, Green Chemistry (Jan. 7, 2014), 16(4) pp. 2190-2196.
Egami and Katsuki, Fe(salan)-catalyzed asymmetric oxidation of sulfides with hydrogen peroxide in water, Journal of the American Chemical Society (2007), 129(29) pp. 8940-8941.
International Search Report and Written Opinion for International Application No. PCT/IB2014/064308, dated Apr. 15, 2015.
Ishii et al., Selectivity in oxidation of sulfides with hydrogen peroxide by [π-C5H5N+(CH2)15CH3]3PM12O403- and [π-C5H5N+(CH2)15CH3]3{PO4[M(O)(O2)2]4}3- (M=Mo or W), Chemistry Letters (Jan. 1994), 1(1) pp. 1-4.
Jeyakumar and Chand, Selective oxidation of sulfides to sulfoxides and sulfones at room temperature using H2O2 and a Mo(VI) salt as catalyst, Tetrahedron Letters (Jul. 3, 2006), 47(27) pp. 4573-4576.
Liu et al., A simple and environmentally benign method for sulfoxidation of sulfides with hydrogen peroxide, Ind. Eng. Chem. Res. (2010), 49(5) pp. 2533-2536.
Noyori et al., Green oxidation with aqueous hydrogen peroxide, Chemical Communications, (16) pp. 1977-1986.
Prasanth and Maheswaran, Selective oxidation of sulfides to sulfoxides in water using 30% hydrogen peroxide catalyzed with a recoverable VO(acac)2 exchanged sulfonic acid resin catalyst, Journal of Molecular Catalysis A: Chemical (May 1, 2007), 268(1-2) pp. 45-49.
Sato et al., Oxidation of sulfides to sulfoxides and sulfones with 30% hydrogen peroxide under organic solvent- and halogen-free conditions, Tetrahedron (Mar. 26, 2001), 57(13) pp. 2469-2476.
Scarso and Strukul, Asymmetric Sulfoxidation of Thioethers With Hydrogen Peroxide in Water Mediated by Platinum Chiral Catalyst, Advanced Synthesis & Catalysis (Jul. 2005), 347(9) pp. 1227-1234.
Schwendt et al., Tetraalkylanmonium Oxalatooxoperoxovanadates, Chemical Papers (1993), 47(5) pp. 288-291.
Zhang et al., Metallomicellar supramolecular systems and their applications in catalytic reactions, Coordination Chemistry Reviews (Sep. 2009), 253(17-18) pp. 2166-2177.

* cited by examiner

SULFOXIDATION CATALYSTS AND METHODS FOR THEIR PREPARATION AND USE

CROSS-REFERENCE TO RELATED APPLICATIONS

This application is a U.S. National Stage filing under 35 U.S.C. § 371 of International Application No. PCT/IB2014/064308, filed on Sep. 8, 2014, and entitled "SULFOXIDATION CATALYSTS AND METHODS FOR THEIR PREPARATION AND USE," which claims the priority benefit of Indian Application No. 4639/CHE/2013, filed on Oct. 15, 2013. The contents of each of these applications are incorporated herein by reference in their entireties.

BACKGROUND

Oxidation is one of the fundamental reactions in organic synthesis. Importantly, sulfoxidation receives special attention in the pharmaceutical chemistry since many sulfoxides are present as active pharmaceutical ingredients. Sulfoxides also act as intermediates for various organic reactions. Sulfoxidation can be achieved using peracids or halogen derivatives as oxidants in an organic medium. However, this method involves using stoichiometric oxidants that generally produce undesirable side products, usually originating from the oxidants.

Sulfoxidation can also be achieved using hydrogen peroxide as an oxidant in an organic medium. This method involves using environmentally benign hydrogen peroxide along with several transition metals. However, the use of low volatile organic solvents as a reaction medium makes it less attractive due to the environmental factor and cost. Sulfoxidation can further be achieved by using hydrogen peroxide as an oxidant in an aqueous medium.

The use of hydrogen peroxide provides an alternative environmentally friendly process that uses water as a reaction medium. Transition metal catalyzed reactions in a pure aqueous medium with hydrogen peroxide as an oxidant makes the methodology attractive in the development of "Green Chemistry" processes. However, the drawback of this method is the difficulty in designing stable catalysts that are soluble in water. Hence, there is an unmet need to develop simple, cost effective, and environment friendly sulfoxidation catalysts that function in an aqueous medium.

SUMMARY

The present disclosure provides, among other things, catalysts and sulfoxidation processes carried out in aqueous medium. In one embodiment, a compound of formula I is disclosed.

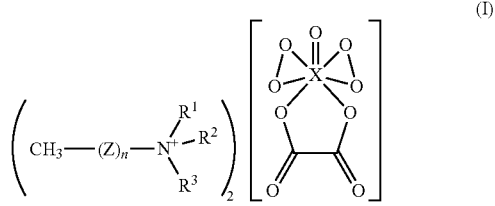
(I)

wherein Z is alkylene, substituted alkylene, arylene, substituted arylene, alkenylene, substituted alkenylene, alkynylene, substituted alkynylene, or any combination thereof;

$R^1$ is alkyl, aryl, alkenyl, alkynyl, or any combination thereof; $R^2$ is alkyl, aryl, alkenyl, alkynyl, or any combination thereof; $R^3$ is alkyl, aryl, alkenyl, alkynyl, or any combination thereof; n is an integer from 1 to 20; and X is Mo, W, V, or Cr.

In another embodiment, a method of making a catalyst may include: contacting a transition metal compound with an oxidizing agent to form a first solution; contacting a carboxylic acid compound with a cationic surfactant to form a second solution; mixing the first solution and the second solution to form a precipitate; and isolating the precipitate.

In an yet another embodiment, a sulfoxidation process may include: contacting a sulfide with a catalyst to form a first reaction mixture; contacting an oxidizing agent with the first reaction mixture to form a second reaction mixture; and isolating a product from the second reaction mixture.

In a further embodiment, a composition may include at least one catalyst and one or more of the following: at least one sulfide and at least one sulfoxide, and wherein the catalyst is represented by a compound of formula I.

DETAILED DESCRIPTION

Figure 1:
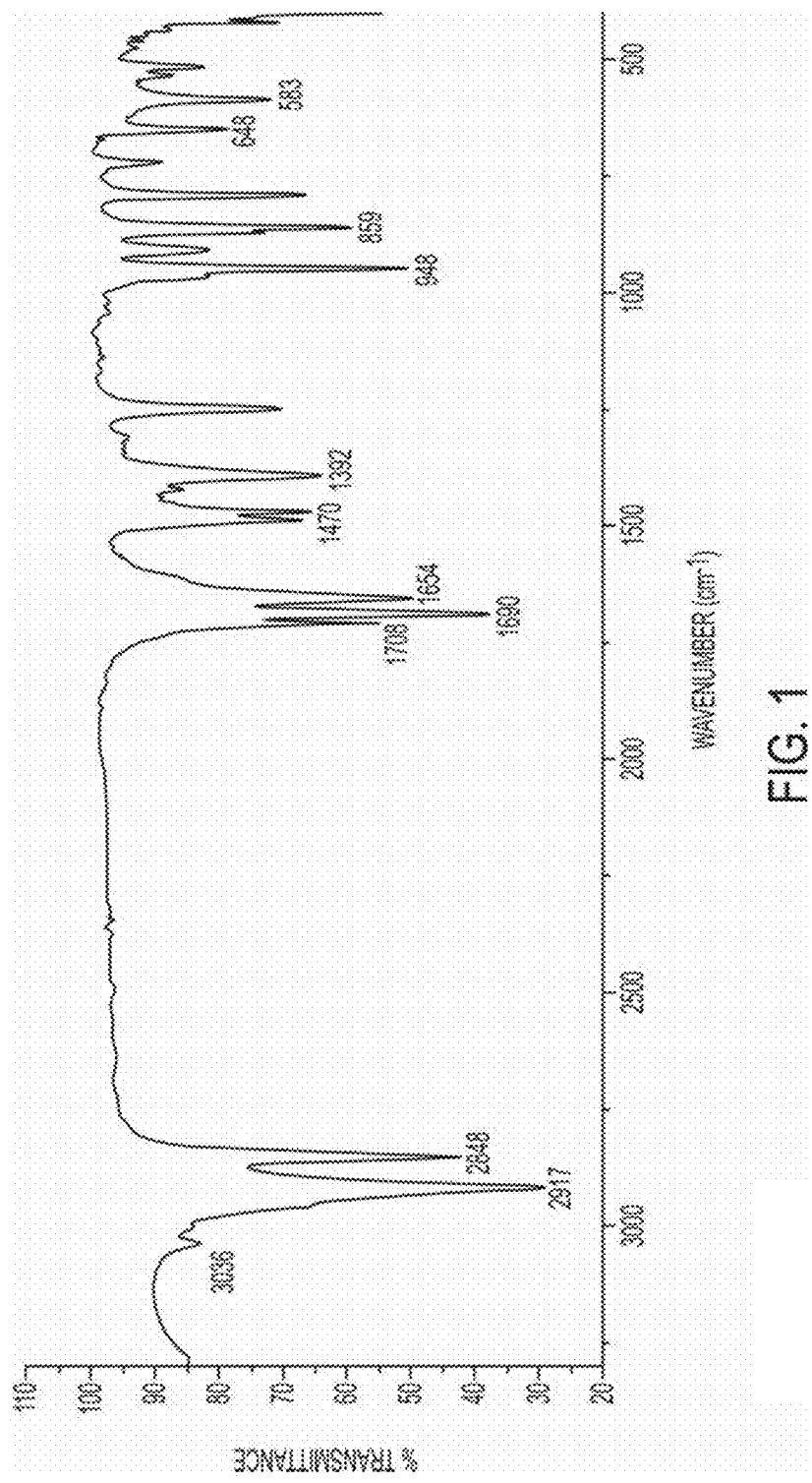
FIG. 1 depicts an IR spectrum of compound 1.

This disclosure is not limited to the particular systems, devices and methods described, as these may vary. The terminology used in the description is for the purpose of describing the particular versions or embodiments only, and is not intended to limit the scope.

"Alkyl" means a saturated hydrocarbon group which is straight-chained or branched. An alkyl group can contain from 1 to 20 carbon atoms, from 2 to 20 carbon atoms, from 1 to 10 carbon atoms, from 2 to 10 carbon atoms, from 1 to 8 carbon atoms, from 2 to 8 carbon atoms, from 1 to 6 carbon atoms, from 2 to 6 carbon atoms, from 1 to 4 carbon atoms, from 2 to 4 carbon atoms, from 1 to 3 carbon atoms, or 2 or 3 carbon atoms. Examples of alkyl groups include, but are not limited to, methyl (Me), ethyl (Et), propyl (e.g., n-propyl and isopropyl), butyl (e.g., n-butyl, t-butyl, isobutyl), pentyl (e.g., n-pentyl, isopentyl, neopentyl), hexyl, isohexyl, heptyl, 4,4 dimethylpentyl, octyl, 2,2,4-trimethylpentyl, nonyl, decyl, undecyl, dodecyl, 2-methyl-1-propyl, 2-methyl-2-propyl, 2-methyl-1-butyl, 3-methyl-1-butyl, 2-methyl-3-butyl, 2-methyl-1-pentyl, 2,2-dimethyl-1-propyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, and the like.

"Alkylene" refers to a bivalent alkyl moiety having the general formula —$(CH_2)_n$—, where n is from about 1 to about 25, about 1 to about 20, or about 4 to about 20. By bivalent, it is meant that the group has two open sites each of which bonds to another group. Non-limiting examples include methylene, ethylene, trimethylene, pentamethylene, and hexamethylene. Alkylene groups can be substituted or unsubstituted, linear or branched bivalent alkyl groups.

"Alkenyl" means a straight or branched alkyl group having one or more double carbon-carbon bonds and 2-20 carbon atoms, including, but not limited to, ethenyl, 1-propenyl, 2-propenyl, 2-methyl-1-propenyl, 1-butenyl, 2-butenyl, and the like. In some embodiments, the alkenyl chain is from 2 to 10 carbon atoms in length, from 2 to 8 carbon atoms in length, from 2 to 6 carbon atoms in length, or from 2 to 4 carbon atoms in length.

"Alkenylene" refers to a divalent alkenyl moiety, meaning the alkenyl moiety is attached to the rest of the molecule at two positions. Alkenylene groups can be substituted or unsubstituted, linear or branched bivalent alkenyl groups.

"Alkynyl" means a straight or branched alkyl group having one or more triple carbon-carbon bonds and 2-20 carbon atoms, including, but not limited to, acetylene, 1-propylene, 2-propylene, and the like. In some embodiments, the alkynyl chain is 2 to 10 carbon atoms in length, from 2 to 8 carbon atoms in length, from 2 to 6 carbon atoms in length, or from 2 to 4 carbon atoms in length.

"Alkynylene" refers to a divalent alkynyl moiety, meaning the alkynyl moiety is attached to the rest of the molecule at two positions. Alkynylene groups can be substituted or unsubstituted, linear or branched bivalent alkynyl groups.

"Arylene" means a bivalent aryl group that links one group to another group in a molecule. Arylene groups may be substituted or unsubstituted.

Catalysts

A challenge to carry out sulfoxidation in an aqueous medium is the solubility of metal catalysts and reactants. The present application discloses surfactant metal catalysts that may be used to carry out various reactions in water. Surfactant metal complexes are amphiphiles having polar heads and non-polar tails. They can form self-assembled dynamic aggregates called "metallo-micelles" and help in solubilizing the organic molecules in aqueous medium. In some embodiments, a compound is of formula I:

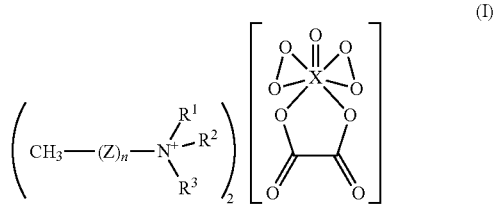

wherein Z may be alkylene, substituted alkylene, arylene, substituted arylene, alkenylene, substituted alkenylene, alkynylene, substituted alkynylene, or any combination thereof; $R^1$ may be alkyl, aryl, alkenyl, alkynyl, or any combination thereof; $R^2$ may be alkyl, aryl, alkenyl, alkynyl, or any combination thereof; $R^3$ may be alkyl, aryl, alkenyl, alkynyl, or any combination thereof; n is an integer from 1 to 20; and X may be Mo, W, V, or Cr.

In some embodiments, Z may be alkylene, alkenylene, or alkynylene. In some embodiments, Z may be —$(CH_2)_{15}$—. In some embodiments, $R^1$ may be alkyl, $R^2$ may be alkyl, and $R^3$ may be alkyl. In some embodiments, $R^1$ may be —$CH_3$, $R^2$ may be —$CH_3$, and $R^3$ may be —$CH_3$.

Examples of metal catalysts represented by formula I include, but are not limited to, the following compounds:

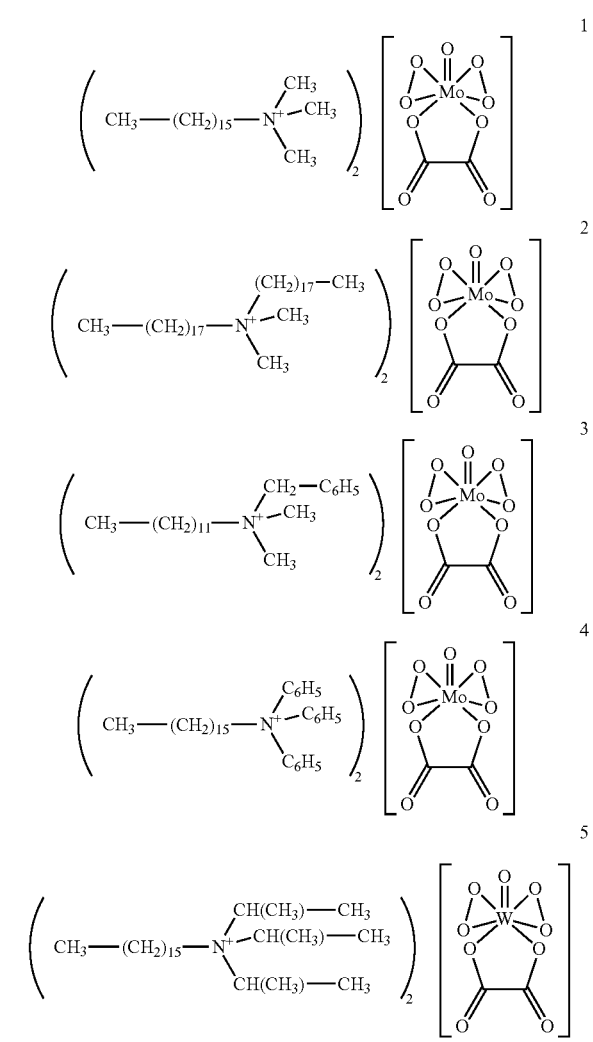

In some embodiments, a method of making a catalyst include contacting a transition metal compound with an oxidizing agent to form a first solution, contacting a carboxylic acid compound with a cationic surfactant to form a second solution, mixing the first solution and the second solution to form a precipitate, and isolating the precipitate.

In some embodiments, the transition metal compound may be a molybdate compound, a vanadate compound, a chromate compound, or a tungsten compound. Non-limiting examples include sodium molybdate, potassium molybdate, calcium molybdate, sodium vanadate, potassium vanadate, calcium vanadate, sodium chromate, potassium chromate, and the like.

In some embodiments, the oxidizing agent may generally be any oxidizing agent, such as potassium persulfate, ammonium persulfate, hydrogen peroxide, benzoyl peroxide, di-tert-butyl peroxide, decanoyl peroxide, lauroyl peroxide, perbenzoic acid, peracetic acid, performic acid, monoperphthalic acid an alkylhydroperoxide derivative, or any combination thereof.

In some embodiments, carboxylic acid may generally be any monocarboxylic acid or polycarboxylic acid, such as oxalic acid, malonic acid, benzoic acid, a pyridine carboxylic acid, lactic acid, maleic acid, succinic acid, glutaric acid, adipic acid, pimelic acid, azelaic acid, sebacic acid, fumaric acid, or any combination thereof.

In some embodiments, the cationic surfactant may generally be any cationic surfactant, such as dimethyl dioctadecyl ammonium chloride, alkyldimethylbenzylammonium chloride, cetyltrimethyl ammonium bromide, cetyltrimethyl ammonium chloride, benzethonium chloride, or any combination thereof.

In some embodiments, the synthesis of a catalyst may be carried out by contacting the transition metal compound with the oxidizing agent to form a first solution. In some embodiments, the transition metal compound and the oxidizing agent may be contacted in generally any molar ratio, such as a molar ratio of about 1:10 to about 1:20, about 1:10 to about 1:16, about 1:10 to about 1:14, or about 1:10 to about 1:12. Specific examples include about 1:10, about 1:12, about 1:15, about 1:18, about 1:20, and ranges between any two of these values (including their endpoints). In some embodiments, the transition metal compound may be contacted with the oxidizing agent in its solid form. In some embodiments, the transition metal compound may be dissolved in water and adjusted to a low pH such as a pH of about 1 to about 4 and then contacted with the oxidizing agent. When the transition metal compound and the oxidizing agent are mixed, the pH of the resulting solution is kept acidic and may be in the range of about pH 1 to about pH 4, about pH 1 to about pH 3, or about pH 1 to about pH 2. Specific examples include, but are not limited to, about pH 1, about pH 1.5, about pH 2, about pH 2.5, about pH 3, about pH 3.5, about pH 4, and ranges between any two of these values (including their endpoints). The pH of the solution may be adjusted by adding sulfuric acid, hydrochloric acid, and the like.

In some embodiments, a second solution is obtained by contacting the carboxylic acid with the cationic surfactant in generally any molar ratio, such as a molar ratio of about 1:1 to about 1:3, about 1:1 to about 1:2, or about 1:1 to about 1:1.5. Specific examples include about 1:1, about 1:1.5, about 1:2, about 1:2.5, about 1:3, and ranges between any two of these values (including their endpoints).

In some embodiments, the first solution and the second solution are mixed by adding the first solution drop-wise into the second solution. Alternatively, the first solution and second solution can be mixed in portions, continuously, or all at once. In some embodiments, the second solution may be added drop-wise into the first solution. In some embodiments, the first solution is added to the cold second solution with mixing. In other embodiments, both the first and second solutions may be mixed together simultaneously. During mixing, the pH of the solution may be maintained below about pH 4. When the first solution and the second solution are mixed, a precipitate may be formed. The precipitate may be isolated by any method known in the art, such as centrifugation, filtration, decantation, and the like. The precipitate obtained may be washed repeatedly with one or more solvents, such as water, diethyl ether, ethyl acetate, methyl alcohol, n-propyl alcohol, isopropyl alcohol, or any combination thereof. The precipitate may be further dried to obtain the catalyst in an isolated form.

In some embodiments, the process of making the catalyst may be carried out in a "one-pot" reaction, by sequential addition of the reactants.

Sulfoxidation

The catalyst obtained as described herein may be used in the sulfoxidation reactions that are carried out in an aqueous medium. In some embodiments, non-aqueous mediums may also be used. In some embodiments, the sulfoxidation process may be carried out by contacting a sulfide with a catalyst to form a first reaction mixture, contacting an oxidizing agent with the first reaction mixture to form a second reaction mixture, and isolating a product from the second reaction mixture.

In some embodiments, the sulfide may be a thiophene derivative, an alkyl sulfide, an aryl sulfide, a substituted aryl sulfide, a cyclic alkyl sulfide, or a combination thereof. The sulfide may be any organic compound having a divalent sulfur atom. The aromatic or heterocyclic groups in these compounds may contain any organic or inorganic substituents, and may be fused to any number of carbocyclic or heterocyclic rings which may be further substituted. Non-limiting examples of substituents include hydroxy, alkoxy, nitro, halo, alkyl, aryl, carboxyl, amido, acyloxy, nitrile, acyl, alkene, oxime, aldehyde, imine, cyano, acetal, amino, and the like.

In some embodiments, during the reaction, the catalyst described herein may selectively oxidize the sulfur group, without altering other substituents. For example, alkene, oxime, aldehyde, imine, acetal, amino, hydroxyl, and cyano functional groups may not be modified during the reaction process (see Table 1).

In some embodiments, the catalyst may be any one of the compounds of formula I described herein.

In some embodiments, the oxidizing agent may be potassium persulfate, ammonium persulfate, hydrogen peroxide, benzoyl peroxide, di-tert-butyl peroxide, decanoyl peroxide, lauroyl peroxide, perbenzoic acid, peracetic acid, performic acid, monoperphthalic acid an alkylhydroperoxide derivative, or any combination thereof.

In some embodiments, the sulfide and the catalyst described herein (formula I) may be mixed in water, to form a first reaction mixture. The mixing can be performed at various temperatures, such as at about 15° C. to about 50° C., about 15° C. to about 40° C., about 15° C. to about 30° C. or about 15° C. to about 20° C. Specific examples include about 15° C., about 20° C., about 25° C., about 30° C., about 40° C., about 50° C., and ranges between any two of these values (including their endpoints).

In some embodiments, an oxidant is mixed with the first reaction mixture to obtain a second reaction mixture, and the reaction is continued. In some embodiments, contacting an oxidizing agent with the first reaction mixture is performed by mixing. The second reaction mixture may be mixed for a period of time, such as about 10 minutes to about 6 hours to obtain the product. The mixing may be performed for various periods of time, such as about 10 minutes to about 6 hours, about 10 minutes to about 4 hours, about 10 minutes to about 2 hours, or about 10 minutes to about 1 hour. Specific examples include about 10 minutes, about 30 minutes, about 1 hour, about 2 hours, about 3 hours, about 4 hours, about 6 hours, and ranges between any two of these values (including their endpoints). The mixing can be performed at various temperatures, such as at about 15° C. to about 50° C., about 15° C. to about 40° C., about 15° C. to about 30° C. or about 15° C. to about 20° C. Specific examples include about 15° C., about 20° C., about 25° C., about 30° C., about 40° C., about 50° C., and ranges between any two of these values (including their endpoints).

In some embodiments, the method can be carried out as a "one-pot" reaction to obtain the product.

The amount of the catalyst and the oxidizing agent used in the process may vary depending on the sulfide. Some sulfides may require low catalytic loading and some sulfides may require high catalytic loading. In some embodiments, the catalyst may be present in the second reaction mixture at generally any concentration, such as about 1 mole percent to about 10 mole percent, about 1 mole percent to about 8 mole percent, about 1 mole percent to about 4 mole percent, or about 1 mole percent to about 2 mole percent. Specific examples include about 1 mole percent, about 2.5 mole percent, about 5 mole percent, about 7 mole percent, about 10 mole percent, and ranges between any two of these values (including their endpoints).

In some embodiments, an oxidizing agent may be present in the second reaction mixture at generally any concentration, such as at about 40 mole percent to about 60 mole percent, about 40 mole percent to about 55 mole percent, about 40 mole percent to about 50 mole percent, or about 40 mole percent to about 45 mole percent. Specific examples include about 40 mole percent, about 45 mole percent, about 50 mole percent, about 55 mole percent, about 60 mole percent, and ranges between any two of these values (including their endpoints).

In some embodiments, the sulfide may be present in the second reaction mixture at generally any concentration, such as at about 30 mole percent to about 60 mole percent, about 30 mole percent to about 55 mole percent, about 30 mole percent to about 50 mole percent, or about 30 mole percent to about 40 mole percent. Specific examples include about 30 mole percent, about 40 mole percent, about 45 mole percent, about 50 mole percent, about 55 mole percent, about 60 mole percent, and ranges between any two of these values (including their endpoints).

A typical sulfoxidation reaction catalyzed by the compound of formula I is represented below:

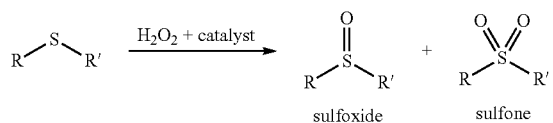

Figure 6:
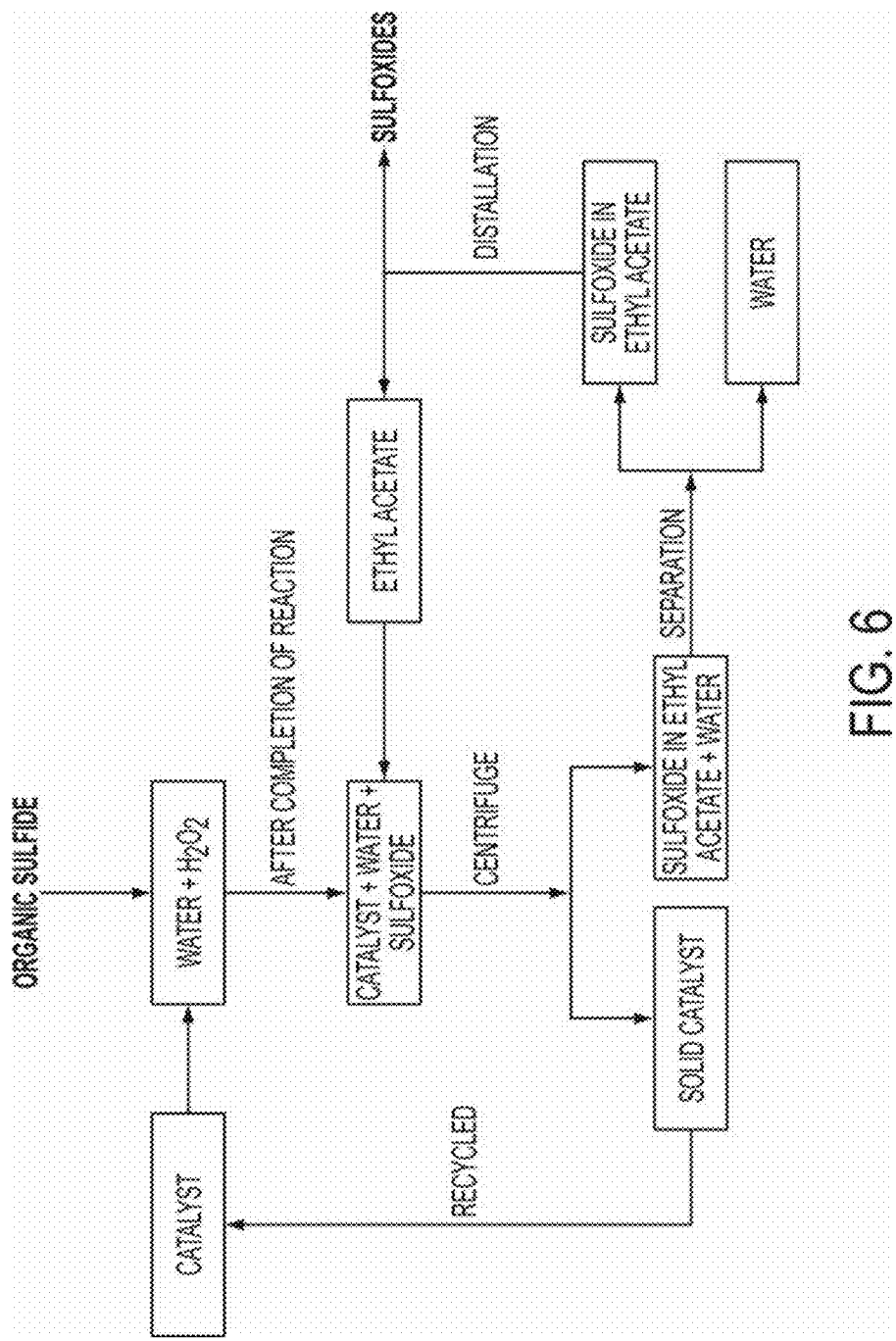
FIG. 6 depicts various steps of a sulfoxidation reaction, and recovery of the catalyst and products, according to an embodiment.

In some embodiments, the product optionally may be isolated at the end of the reaction by adding at least one organic solvent to the second reaction mixture. Non-limiting examples of the organic solvent may be methylene chloride, tetrahydrofuran, methanol, ethanol, propanol, ether, acetone, ethyl acetate, or any combination thereof. In some embodiments, the catalyst may be recovered from the reaction mixture and recycled. This may be performed by centrifugation, filtration, or any known chromatography techniques, and the recovered catalyst may be re-used again. Once the catalyst is separated, the products of the sulfoxidation reaction (sulfoxides and sulfones) may be isolated by extracting the solvent from the aqueous phase, and products recovered from the organic solvent. Several examples of recovery and purification methods are distillation, sublimation, crystallization, chromatography, filtration, and Soxhlet-type extraction. The organic solvent may optionally be re-used in the reaction process. FIG. 6 illustrates various steps involved in sulfoxidation process, including recycling of the catalyst and the organic solvent.

The metallo-micellar catalysts described herein are developed for various reactions, such as room temperature, sulfoxidation reactions that are carried out in aqueous medium. In addition, these catalysts can also be used for sulfoxidation reactions carried out in organic solvents, and at high temperatures. Several other advantages of the methods described herein are high chemoselectivity, easy separation of the product, recyclability of the catalyst and the organic solvent.

EXAMPLES

Example 1

Synthesis of Compound 1

Solution A: A 5 mL volume of 160 mM sodium molybdate dihydrate was diluted with 5 mL of water. The acidity of the solution was adjusted to pH 2 with 0.1 M sulfuric acid. About 1 mL of 36% (v/v) hydrogen peroxide was added and the resulting solution was diluted to 20 mL with water. Solution B: Oxalic acid dihydrate (0.106 grams) was added into 2.5 mL of an aqueous solution of cetyl trimethyl ammonium bromide (0.604 grams) and the resulting solution was diluted to 5 mL with water. In an ice-cold condition with vigorous stirring, solution A was added dropwise into solution B and the pH of the resulting solution was maintained at pH 2 by adding sulfuric acid. After 5 minutes, the formation of bright yellow precipitate was observed. The reaction mixture was centrifuged, and the precipitate was washed 2-3 times with water and dried under vacuum (yield of compound 1 was 82%).

Figure 2:
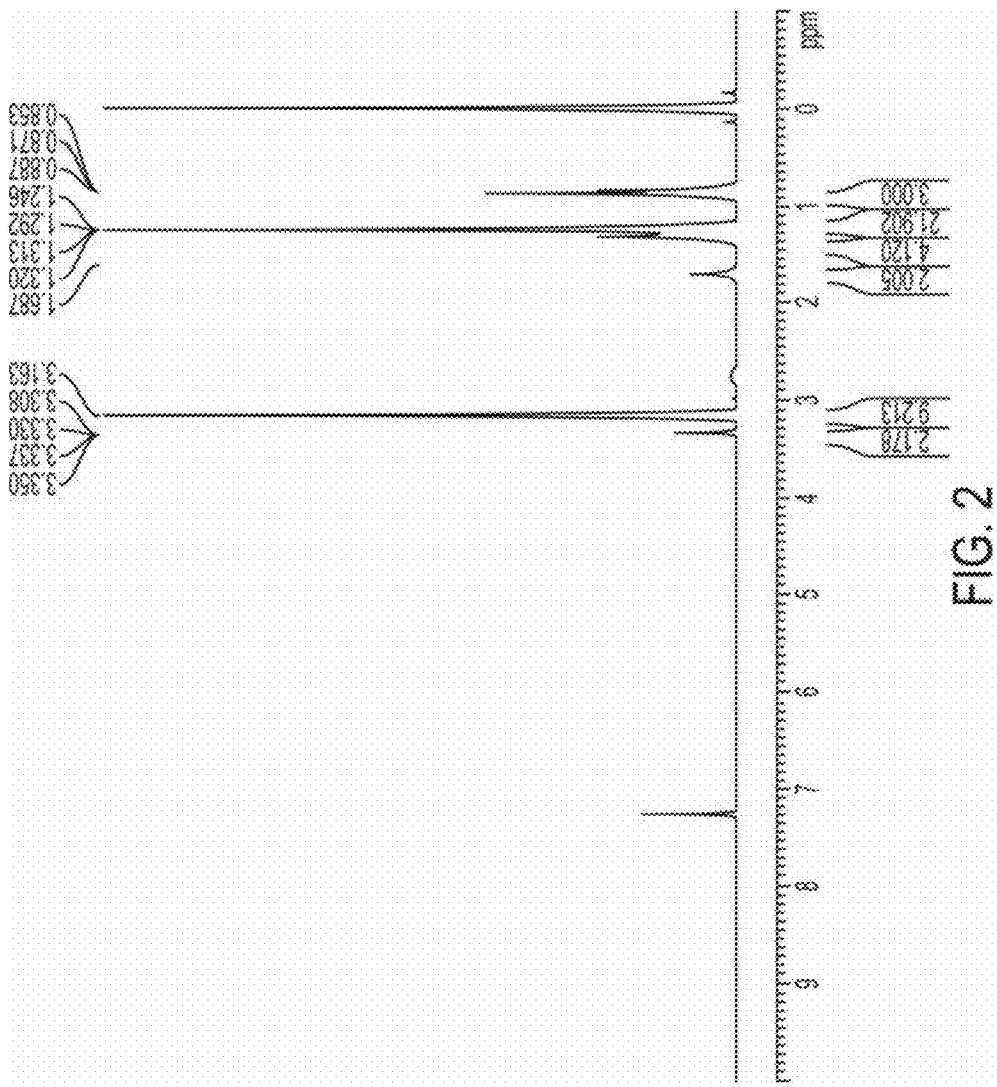
FIG. 2 depicts a $^1$H-NMR spectrum of compound 1.
Figure 3:
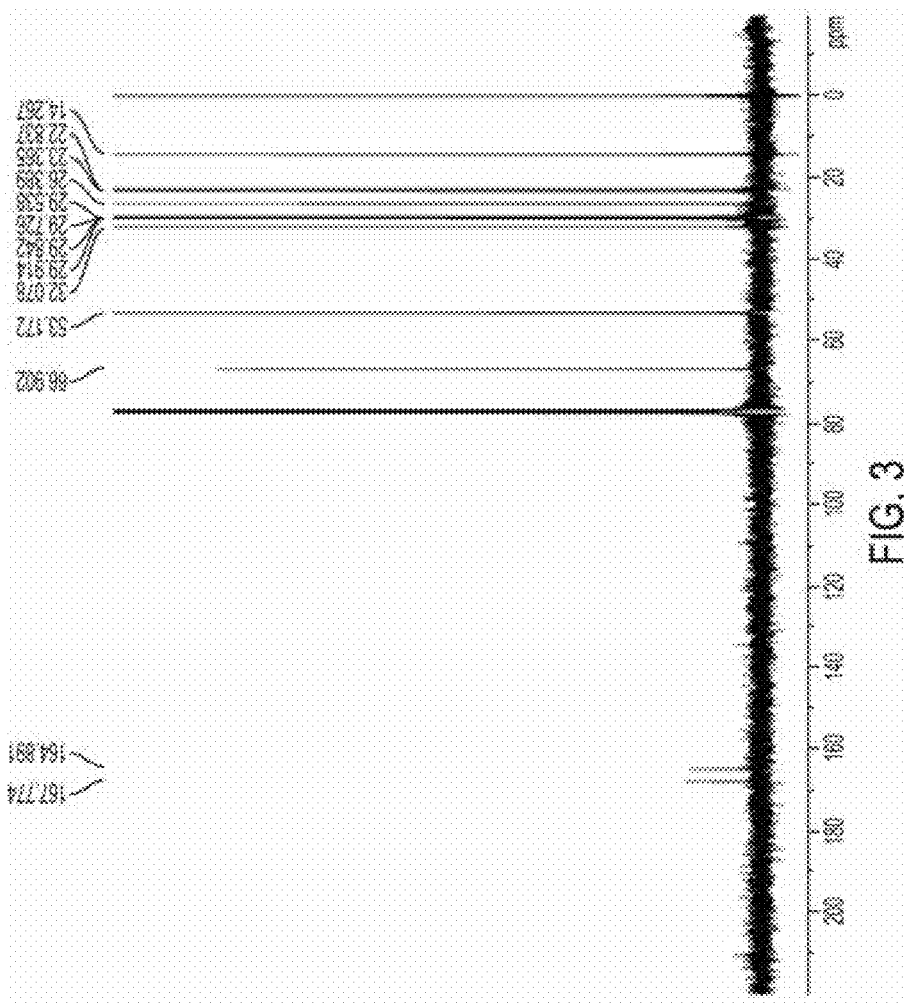
FIG. 3 shows $^{13}$C-NMR spectrum of compound 1.
Figure 4:
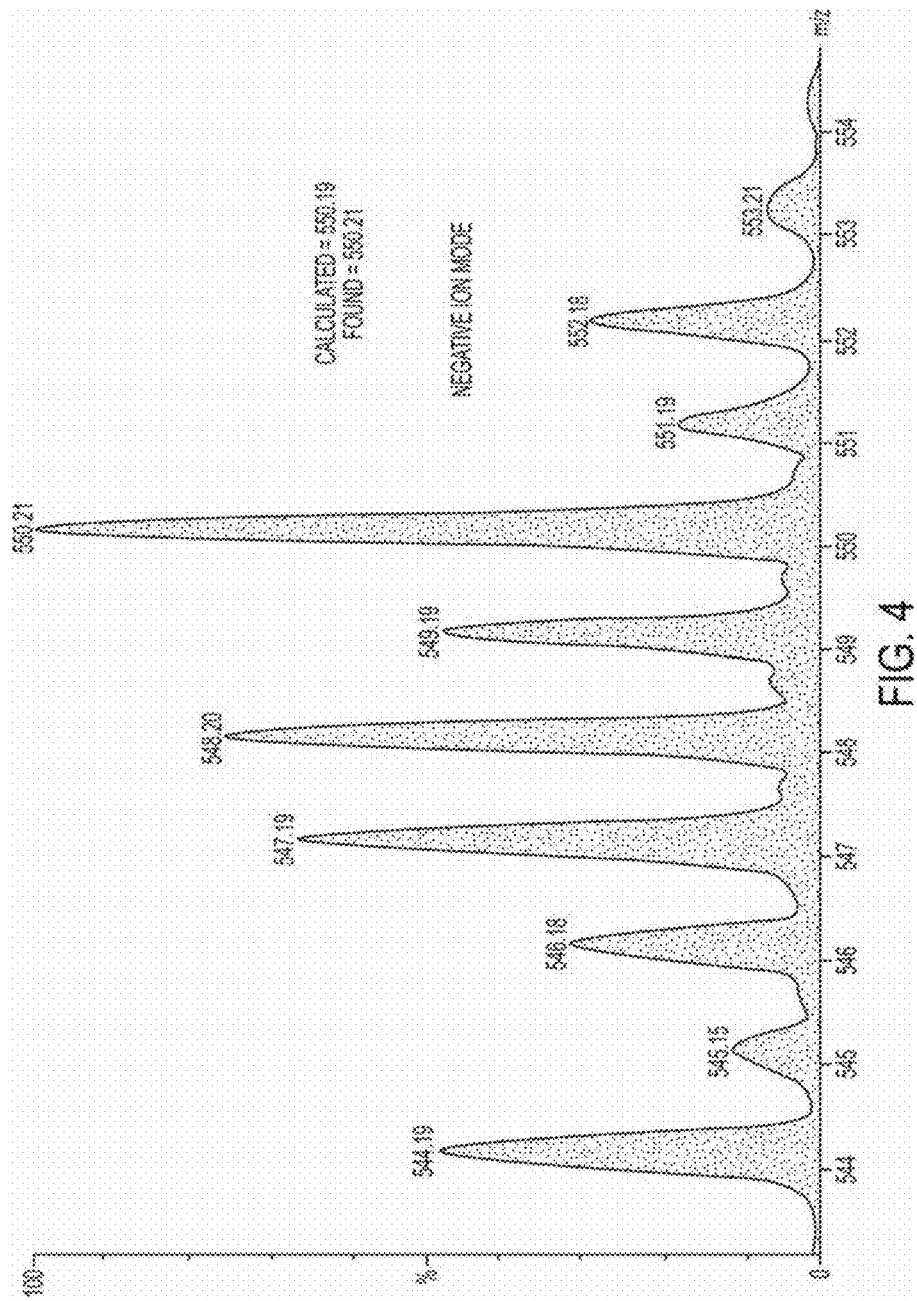
FIG. 4 shows ESI-MS spectrum of compound 1.
Figure 5:
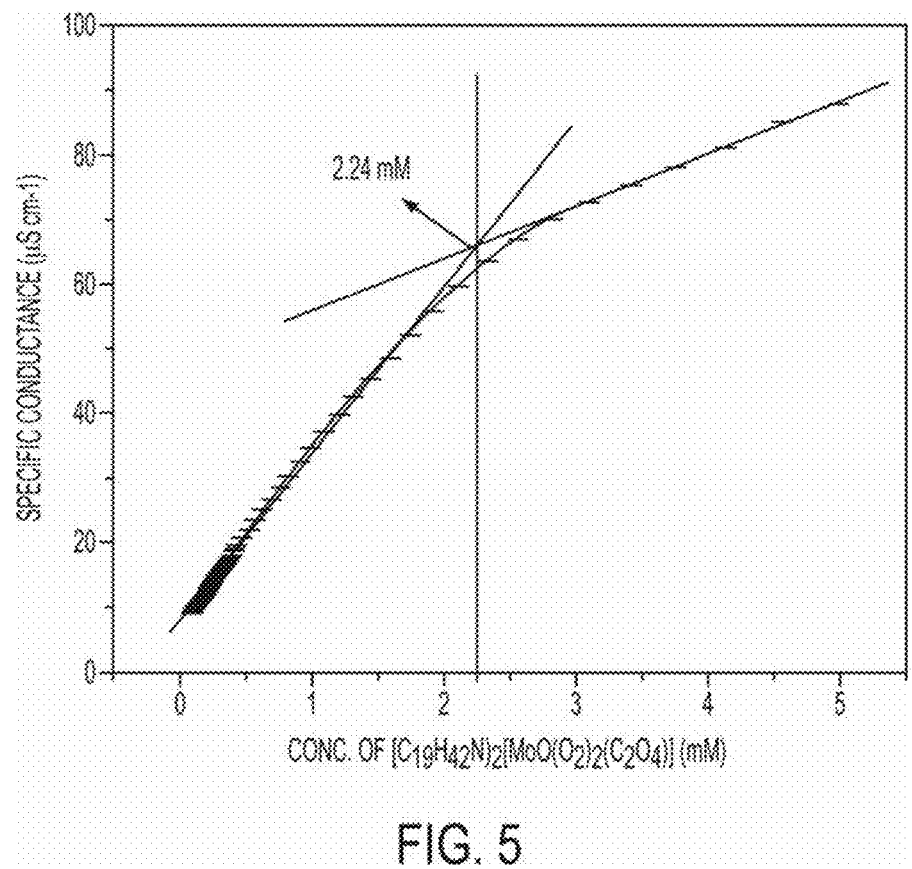
FIG. 5 shows the critical micellar concentration of compound 1.

The infrared spectrum (FIG. 1) was recorded and the significant frequencies for the formation of per-oxo complexes were compared. The sharp and strong peaks at 948 $cm^{-1}$ and 859 $cm^{-1}$ represent the vibration of $v(Mo=O)$ and $v(O-O)$. The vibration band around 1708-1654 $cm^{-1}$ and 1470 $cm^{-1}$ represent numerous vibrational modes of oxalate groups. The peaks at 648 $cm^{-1}$ and 583 $cm^{-1}$ represent $v(Mo(O_2))$ stretches. The $^1$H-NMR spectrum of compound 1 was recorded in $CDCl_3$ solvents. The spectrum displays the peaks for cetyl trimethyl ammonium moiety with correct integration ratio (FIG. 2). The $^{13}$C-NMR data displayed also supported for the formation of the complex (FIG. 3). Electrospray ionization-mass spectrometry (ESI-MS) study was carried out for the complex in acetonitrile:chloroform solvent mixture. Molecular ion peaks obtained are depicted in FIG. 4. Critical micellar concentration of compound 1 was determined by conductivity method and was found to be 2.24 mM (FIG. 5).

Example 2

Synthesis of Compound 2

Solution A: A 5 mL volume of 160 mM sodium molybdate dihydrate is diluted with 5 mL of water. The acidity of the solution is adjusted to pH 2 with 0.1 M sulfuric acid. About 1 mL of 36% hydrogen peroxide is added and the resulting solution is diluted to 20 mL with water. Solution B: Oxalic acid dihydrate (0.106 grams) is added into 2.5 ml of an aqueous solution of dimethyl dioctadecyl ammonium chloride (0.960 grams) and the resulting solution is diluted to 5 mL with water. In an ice-cold condition with vigorous stirring, solution A is added dropwise into solution B and the pH of the resulting solution is maintained at pH 2 by adding sulfuric acid. After 5 minutes, the formation of the precipitate is observed. The reaction mixture is centrifuged and the precipitate is washed 2-3 times with water and dried under vacuum (yield of compound 2 was 84%).

Example 3

Synthesis of compound 3

Solution A: A 5 mL volume of 160 mM sodium molybdate dihydrate is diluted with 5 mL of water and the acidity of the solution is adjusted to pH 2 with 0.1 M sulfuric acid. About 1 mL of 36% hydrogen peroxide is added and the resulting solution is diluted to 20 mL with water. Solution B: Oxalic acid dihydrate (0.106 grams) is added into 2.5 ml of an aqueous solution of alkyldimethylbenzylammonium chloride (0.604 grams) and the resulting solution is diluted to 5 mL with water. In an ice-cold condition with vigorous stirring, solution A is added dropwise into solution B and the pH of the resulting solution is maintained at pH 2 by adding sulfuric acid. After 5 minutes, the formation of the precipitate is observed. The reaction mixture is centrifuged and the precipitate is washed 2-3 times with water and dried under vacuum (yield of compound 3 was 85%).

Example 4

Sulfoxidation Reaction of Thioanisole to Methylsulfinyl Benzene

A mixture of compound 1 (2.5 mol %) and thioanisole (1.5 mmol) in 2.5 mL of water was stirred at room temperature. 30% hydrogen peroxide (1.5 mmol) was added slowly into the reaction mixture, and stirring was continued for 30 minutes. Reaction progress was monitored by TLC. After completion, ethyl acetate was added to it and the reaction mixture was centrifuged and decanted to separate the molybdenum compound. The aqueous phase was extracted with ethyl acetate 3-4 times. The organic layer was distilled to obtain methylsulfinyl benzene.

Example 5

Sulfoxidation Reactions

Sulfoxidation reactions were performed in aqueous medium as in Example 4 with various sulfides, using compound 1 as a catalyst and $H_2O_2$ as an oxidant. The resulting sulfoxides are depicted in Table 1. These results show that high yields are easily attained in short periods of time by using the sulfoxidation catalysts.

TABLE 1

| Entry | Sulfides | Sulfoxides | Time | Yields |
|---|---|---|---|---|
| 1 | 1a | 1b | 30 min | 95% |
| 2 | 2a | 2b | 20 min | 85% |
| 3 | 3a | 3b | 10 min | 91% |
| 4 | 4a | 4b | 30 min | 93% |

TABLE 1-continued

| Entry | Sulfides | Sulfoxides | Time | Yields |
|---|---|---|---|---|
| 5 | 4-methoxyphenyl methyl sulfide (5a) | 4-methoxyphenyl methyl sulfoxide (5b) | 30 min | 94% |
| 6 | 2-chlorophenyl methyl sulfide (6a) | 2-chlorophenyl methyl sulfoxide (6b) | 2 h | 90% |
| 7 | 4-chlorophenyl methyl sulfide (7a) | 4-chlorophenyl methyl sulfoxide (7b) | 1 h | 78% |
| 8 | diallyl sulfide (8a) | diallyl sulfoxide (8b) | 30 min | 92% |
| 9 | 1-(4-(methylthio)phenyl)ethanol (9a) | 1-(4-(methylsulfinyl)phenyl)ethanol (9b) | 20 min | 92% |
| 10 | 4-(methylthio)aniline (10a) | 4-(methylsulfinyl)aniline (10b) | 10 min | 96% |
| 11 | 4-(methylthio)phenol (11a) | 4-(methylsulfinyl)phenol (11b) | 10 min | 90% |

TABLE 1-continued

| Entry | Sulfides | Sulfoxides | Time | Yields |
|---|---|---|---|---|
| 12 | 12a: H₃C-S-C₆H₄-CH₂OH | 12b: H₃C-S(O)-C₆H₄-CH₂OH | 2 h | 75% |
| 13 | 13a: NC-CH₂-S-Ph | 13b: NC-CH₂-S(O)-Ph | 45 min | 71% |
| 14 | 14a: H₃C-S-C₆H₄-CH(OCH₂CH₂CH₂O) (1,3-dioxane) | 14b: H₃C-S(O)-C₆H₄-CH(OCH₂CH₂CH₂O) (1,3-dioxane) | 6 h | 84% |
| 15 | 15a: H₃C-S-C₆H₄-NO₂ | 15b: H₃C-S(O)-C₆H₄-NO₂ | 6 h | 85% |
| 16 | 16a: H₃C-S-C₆H₄-CH=N-Ph | 16b: H₃C-S(O)-C₆H₄-CH=N-Ph | 6 h | 71% |

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

We claim:

1. A method of making a catalyst of formula I:

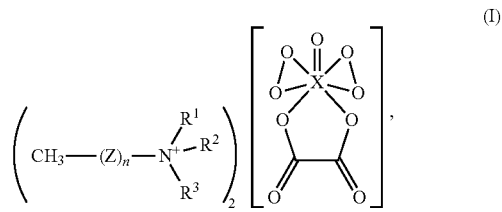

wherein Z is alkylene, arylene, alkenylene, or alkynylene;
$R^1$ is alkyl, aryl, alkenyl, or alkynyl;
$R^2$ is alkyl, aryl, alkenyl, or alkynyl;
$R^3$ is alkyl, aryl, alkenyl, or alkynyl;
n is an integer from 1 to 20; and
X is Mo, V, or Cr, the method comprising:
contacting a transition metal compound with an oxidizing agent to form a first solution;
contacting a carboxylic acid compound with a cationic surfactant to form a second solution;
mixing the first solution and the second solution to form a precipitate; and
isolating the catalyst.

2. The method of claim 1, wherein contacting the transition metal compound comprises contacting a molybdate compound, a vanadate compound, or a chromate compound.

3. The method of claim 1, wherein contacting the carboxylic acid compound comprises contacting oxalic acid, malonic acid, benzoic acid, a pyridine carboxylic acid, lactic acid, maleic acid, succinic acid, glutaric acid, adipic acid, pimelic acid, azelaic acid, sebacic acid, fumaric acid, or any combination thereof.

4. The method of claim 1, wherein contacting the transition metal compound with the oxidizing agent comprises contacting with potassium persulfate, ammonium persulfate, hydrogen peroxide, benzoyl peroxide, di-tert-butyl peroxide, decanoyl peroxide, lauroyl peroxide, perbenzoic acid, peracetic acid, performic acid, monoperphthalic acid, or any combination thereof.

5. The method of claim 1, wherein contacting the carboxylic acid compound with the cationic surfactant comprises contacting with dimethyl dioctadecyl ammonium chloride, alkyldimethylbenzyl ammonium chloride, cetyltrimethyl ammonium bromide, cetyltrimethyl ammonium chloride, benzethonium chloride, or any combination thereof.

6. The method of claim 1, wherein contacting the transition metal compound with the oxidizing agent comprises contacting the transition metal compound with the oxidizing agent in a molar ratio of 1:10 to 1:20.

7. The method of claim 1, wherein contacting the transition metal compound with the oxidizing agent comprises contacting the transition metal compound with the oxidizing agent to form a solution having a pH of 1 to 4.

8. The method of claim 1, wherein contacting the carboxylic acid compound with the cationic surfactant comprises contacting the carboxylic acid compound with the cationic surfactant in a molar ratio of 1:1 to 1:3.

9. The method of claim 1, further comprising maintaining acidity below a pH of 4 during mixing the first solution and the second solution.

10. A sulfoxidation process comprising:
contacting a sulfide with a catalyst of formula I

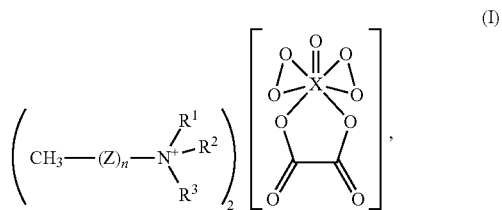

wherein Z is alkylene, arylene, alkenylene, or alkynylene;

$R^1$ is alkyl, aryl, alkenyl, or alkynyl;

$R^2$ is alkyl, aryl, alkenyl, or alkynyl;

$R^3$ is alkyl, aryl, alkenyl, or alkynyl;

n is an integer from 1 to 20; and

X is Mo, V, or Cr, to form a first reaction mixture;

contacting an oxidizing agent with the first reaction mixture to form a second reaction mixture; and isolating a product from the second reaction mixture.

11. The method of claim 10, wherein contacting the sulfide comprises contacting an alkyl sulfide, an aryl sulfide, a substituted aryl sulfide, a cyclic alkyl sulfide, or a combination thereof.

12. The method of claim 10, wherein contacting the oxidizing agent comprises contacting potassium persulfate, ammonium persulfate, hydrogen peroxide, benzoyl peroxide, di-tert-butyl peroxide, decanoyl peroxide, lauroyl peroxide, perbenzoic acid, peracetic acid, performic acid, monoperphthalic acid, or any combination thereof.

13. The method of claim 10, wherein contacting the oxidizing agent comprises contacting with the sulfide present in the second reaction mixture at a concentration of 30 mole percent to 60 mole percent.

14. The method of claim 10, wherein contacting the oxidizing agent comprises contacting with the catalyst present in the second reaction mixture at a concentration of 1 mole percent to 10 mole percent.

15. The method of claim 10, wherein the oxidizing agent is present in the second reaction mixture at a concentration of 40 mole percent to 60 mole percent.

16. The method of claim 10, wherein isolating the product comprises adding at least one organic solvent to the second reaction mixture.

17. The method of claim 16, wherein isolating the product further comprises removing the solvent from the second reaction mixture.

18. The method of claim 10, wherein isolating the product comprises isolating at least one sulfoxide, at least one sulfone, or any combination thereof.

* * * * *